(12) United States Patent
Heidecke et al.

(10) Patent No.: US 10,802,020 B2
(45) Date of Patent: Oct. 13, 2020

(54) DIAGNOSIS OF CHRONIC FATIGUE DISEASES USING DETECTION ANTIBODIES DIRECTED AGAINST A β-ADRENERGIC RECEPTOR

(71) Applicants: CELLTREND GMBH, Luckenwalde (DE); CHARITÉ—UNIVERSITÄTSMEDIZIN BERLIN, Berlin (DE)

(72) Inventors: Harald Heidecke, Berlin (DE); Kai Schulze-Forster, Berlin (DE); Carmen Scheibenbogen, Berlin (DE)

( * ) Notice: Subject to any disclaimer, the term of this patent is extended or adjusted under 35 U.S.C. 154(b) by 123 days.

(21) Appl. No.: 15/576,456

(22) PCT Filed: May 24, 2016

(86) PCT No.: PCT/EP2016/061636
§ 371 (c)(1),
(2) Date: Nov. 22, 2017

(87) PCT Pub. No.: WO2016/188979
PCT Pub. Date: Dec. 1, 2016

(65) Prior Publication Data
US 2018/0156793 A1 Jun. 7, 2018

(30) Foreign Application Priority Data
May 26, 2015 (EP) .................................. 15169232

(51) Int. Cl.
*G01N 33/564* (2006.01)
*G01N 33/68* (2006.01)

(52) U.S. Cl.
CPC ....... *G01N 33/564* (2013.01); *G01N 33/6893* (2013.01); *G01N 2333/726* (2013.01); *G01N 2800/306* (2013.01)

(58) Field of Classification Search
CPC ............. G01N 33/564; G01N 33/6893; G01N 2333/726; G01N 2800/306
See application file for complete search history.

(56) References Cited

U.S. PATENT DOCUMENTS

2005/0049256 A1  3/2005  Lorton et al.

FOREIGN PATENT DOCUMENTS

WO   2010/069570 A2   6/2010
WO   2014/198698 A1   12/2014

OTHER PUBLICATIONS

Scheibenbogen, Carmen et al., "Immunoadsorption to remove β2 adrenergic receptor antibodies in Chronic Fatigue Syndrom CFS/ME", PLOS One, Mar. 15, 2018, pp. 1-15.
Tanaka, Susumu et al., "Autoantibodies against muscarinic cholinergic receptor in chronic fatigue syndrome", International Journal of Molecular Medicine, Aug. 2003, pp. 225-230, vol. 12, No. 2.
Sommerfeldt, Line et al., "Polymorphisms of adrenergic cardiovascular control genes are associated with adolescent chronic fatigue syndrome", Acta Paediatrica, Nov. 18, 2010, pp. 293-298, vol. 100, No. 2.
Loebel, Madlen et al., "Deficient EBV-Specific B- and T-Cell Response in Patients with Chronic Fatigue Syndrome", PLOS ONE, Jan. 15, 2014, pp. 1-10, vol. 9, No. 1.
Loebel, Madlen et al., "Antibodies to β adrenergic and muscarinic cholinergic receptors in patients with Chronic Fatigue Syndrome", Brain, Behavior, and Immunity, Sep. 21, 2015, pp. 32-39, vol. 52.
International Search Report and Written Opinion of International Patent Application No. PCT/EP2016/061636 dated Jul. 28, 2016.

*Primary Examiner* — Ruixiang Li
(74) *Attorney, Agent, or Firm* — McBee Moore & Vanik IP, LLC

(57) ABSTRACT

The application relates to a method for diagnosis of a chronic fatigue disease, e.g. CFS or CRF, comprising the step of determining the presence or absence of antibodies directed against β-adrenergic receptor in a sample of the subject to be diagnosed, wherein the presence of antibodies directed against β-adrenergic receptor is indicative of the chronic fatigue disease in said subject. Furthermore, the application relates to kits comprising β-adrenergic receptor or an antigenic peptide thereof and the use of β-adrenergic receptor or an antigenic peptide thereof for the diagnosis of a chronic fatigue disease.

11 Claims, 2 Drawing Sheets

Specification includes a Sequence Listing.

A

B

A

B

DIAGNOSIS OF CHRONIC FATIGUE DISEASES USING DETECTION ANTIBODIES DIRECTED AGAINST A β-ADRENERGIC RECEPTOR

CROSS-REFERENCE TO RELATED APPLICATIONS

This application is a National Stage entry of International Application No. PCT/EP2016/061636, filed 24 May 2016, which claims priority to European Patent Application No. 15169232.4, filed 26 May 2015. The disclosures of the priority applications are incorporated in their entirety herein by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2905193-022000_ST25.txt" created on 21 Nov. 2017, and 8,263 bytes in size) is concurrently with the instant application, and the entire contents of the Sequence Listing are incorporated herein by reference.

BACKGROUND

Field of the Invention

The present invention is in the field of medicine, in particular to the field diagnostics and prognosis of chronic fatigue, such as chronic fatigue syndrome and chronic tumor fatigue (chronic cancer-related fatigue; CRF). Furthermore, it relates to methods, means and kits for diagnosis chronic fatigue and the detection of antibodies directed against beta-adrenergic receptors in samples of patients.

Description of Related Art

Chronic fatigue is a persistent fatigue that does not relieved by rest. The causes may be differing.

One major group of fatigue is tumor fatigue. Cancer-related fatigue is a subjective symptom of fatigue that is experienced by nearly all cancer patients. Among patients receiving cancer treatment other than surgery, it is essentially universal. Fatigue is a normal and expected side effect of most forms of chemotherapy, radiation therapy, and biotherapy. On average, cancer-related fatigue is "more severe, more distressing, and less likely to be relieved by rest" than fatigue experienced by healthy people. It can range from mild to severe, and may be either temporary or a long-term effect. Fatigue may be a symptom of the cancer, or it may be the result of treatments for the cancer. The National Comprehensive Cancer Network defines cancer-related fatigue as "a distressing persistent, subjective sense of physical, emotional and/or cognitive tiredness or exhaustion related to cancer or cancer treatment that is not proportional to recent activity and interferes with usual functioning". The pathophysiology of cancer-related fatigue is poorly understood. It may be caused by the cancer or the effects it has on the body, by the body's response to the cancer, or by the cancer treatments. Nevertheless, fatigue is a common symptom of cancer. Some fatigue is caused by cancer treatments. This may show a characteristic pattern. For example, people on many chemotherapy regimens often feel more fatigue in the week after treatments, and less fatigue as they recover from that round of medications. People receiving radiation therapy, by contrast, often find their fatigue steadily increases until the end of treatment. Proposed mechanisms by which cancer can cause fatigue include an increase in pro-inflammatory cytokines, deregulation of the hypothalamic-pituitary-adrenal axis, disruption of circadian rhythms, muscle loss and cancer wasting, and genetic problems. Chronic tumor fatigue or chronic cancer related fatigue (CRF) according to the proposed ICD-10 criteria is presently diagnosed, if at least 6 of the following 11 symptoms are present in the patient (see Cella D, et al. Cancer-related fatigue: prevalence of proposed diagnostic criteria in a United States sample of cancer survivors; J Clin Oncol. 2001 Jul. 15; 19(14):3385-91):

1) distinct fatigue, energy loss, or inappropriately increased need for rest affecting daily life;
2) sense of generic weakness or heaviness in one's limbs;
3) concentration disorders;
4) disorder of the short-term memory;
5) disturbed sleep pattern (insomnia or undue need of sleep);
6) unrelaxing sleep;
7) lack of motivation or interest for normal activities of daily routine;
8) the feeling of the need to constrain oneself for every activity;
9) difficulties in the accomplishment of everyday's life;
10) malaise for several hours following on physical exercise;
11) distinct emotional reactions on the felt fatigue (e.g. depressiveness, frustration, testiness).

Most of the patients undergoing tumor/cancer therapy suffer from fatigue during the treatment, e.g. 70 to 80% of tumor patients undergoing chemotherapy or radiation therapy suffer from tumor fatigue. Even though fatigue disappears in most of the patients, about 30% of the patients retain fatigue for more than 12 months, i.e. are suffering from a chronic cancer-related fatigue (CRF; Bower J E; Cancer-related fatigue—mechanisms, risk factors, and treatments. Nat Rev Clin Oncol. 2014 October; 11:597-609. Review 2014). Until today there is no predictive measure for the development of chronic cancer-related fatigue. As CRF is an independent risk factor interfering with post treatment relapse-free and overall survival status in cancer patients (Groenvold et al. Psychological distress and fatigue predicted recurrence and survival in primary breast cancer patients. Breast Cancer Res Treat. 2007; 105(2):209-19; Abraham et al. A nested cohort study of 6,248 early breast cancer patients treated in neoadjuvant and adjuvant chemotherapy trials investigating the prognostic value of chemotherapy-related toxicities. BMC Med. 2015; 13:306) the demand for a diagnosis and prognosis is even higher.

Chronic fatigue syndrome (CFS) is a complex medical condition, characterized by long term fatigue and other symptoms. These symptoms are to such a degree that they limit a person's ability to carry out ordinary daily activities. The fatigue is not due to ongoing exertion, not relieved much by rest, and is not caused by other medical conditions. CFS may also be referred to as systemic exertion intolerance disease (SEID), myalgic encephalomyelitis (ME), post-viral fatigue syndrome (PVFS), chronic fatigue immune dysfunction syndrome (CFIDS), or several other terms. Biological, genetic, infectious, and psychological mechanisms have been proposed, but the cause is not understood until today.

CFS often takes a severe course with further physical and neuro-cognitive symptoms. Symptoms of CFS include malaise after exertion; unrefreshing sleep, widespread muscle and joint pain, sore throat, headaches of a type not previously experienced, cognitive difficulties, chronic and severe mental and physical exhaustion. Additional symptoms may be reported, including muscle weakness, increased sensitivity to light, sounds and smells, problems standing upright, digestive disturbances, depression, painful and often slightly swollen lymph nodes, cardiac and respiratory problems. It is unclear if these symptoms represent other associated conditions or if they are produced by CFS itself. Symptoms vary in number, type, and severity from person to person. Quality of life of persons with CFS can be extremely compromised.

Fatigue is a common symptom in many illnesses, but CFS is comparatively rare. In the USA, over 4 Million people are suffering from CFS, in Germany a prevalence of 0.3% was estimated in a report of the Ministry of Health; see Scheibenbogen et al.; *Chronisches Fatigue-Syndrom. Heutige Vorstellung zur Pathognese, Diagnostik and Therapie*; Hans Marseille Verlage GmbH München; Chir. Praxis, 78:725-732.

Nowadays, no specific diagnostic marker is available and the diagnosis is widely restricted to the clinical symptoms of the patient which can only be conducted by an experienced practitioner. Nevertheless, CFS is often misdiagnosed as depression.

The causes of CFS are heavily discussed. It is believed to be an autoimmune disease with an yet unknown antigen. A B-cell depletion with Rituximab causes remission in half of the patients; see Fluge et al. (2011); *Benefit from B-lymphocyte depletion using the anti-CD20 antibody rituximab in chronic fatigue syndrome. A double-blind and placebo-controlled study*; PLoS One; 6(10):e26358). CFS in most of the cases starts with a viral infection. In about a third of all patients a late Epstein-Barr-Virus (EBV) primary infection can be demonstrated or is least suspected; see Loebel etl al. (2014); *Deficient EBV-specific B-and T-cell response in patients with chronic fatigue syndrome*; PLoS One, 9(1): e85387. EBV is also known to trigger other autoimmune diseases like multiple sclerosis and systemic lupus erythematosus; see Ruprecht, et al. (2014) *Multiple sclerosis: The elevated antibody response to Epstein-Barr virus primarily targets, but is not confined to, the glycine-alanine repeat of Epstein-Barr nuclear antigen*-1; J Neuroimmunol.; 272(1-2): 56-61.

The definition of CFS includes a heterogenic group of diseases that show common or overlapping symptoms. However, until today there is no diagnostic available that could diagnose patients with CFS or even a subgroup of patients.

Until today there is no reliable measure for diagnosis (or prognosis) of the presence of a chronic fatigue disease, like CRF or CFS in a subject.

Hence, there is the long felt need for a diagnostic marker to allow to reliably diagnose CFS, CRF or a subgroup of CFS patients.

SUMMARY OF THE INVENTION

The inventors now found the correlation of the presence of antibodies directed against β-adrenergic receptors and the diagnosis of chronic fatigue disease in a patient. This has in particular been shown for two different chronic fatigue disease, CFS and CRF. The inventors now found that there is a correlation of the presence of antibodies directed against β-adrenergic receptors and the diagnosis of CFS in a patient. The data presented herein demonstrate that auto-antibodies directed against β-adrenergic receptors provide an advantageous tool for diagnosis of CFS patients. The inventors also found that there is a correlation of the presence of antibodies directed against β-adrenergic receptors and the diagnosis of CRF in a patient. The data presented herein demonstrate that auto-antibodies directed against β-adrenergic receptors provide an advantageous tool for diagnosis of CRF patients.

Hence, the present application relates to a method for diagnosis of a chronic fatigue disease, comprising the step of determining the presence or absence of antibodies directed against one or more β-adrenergic receptors in a sample of the subject to be diagnosed, wherein the presence of antibodies directed against one or more β-adrenergic receptors is indicative of the presence of a chronic fatigue disease in said subject.

In a preferred embodiment the chronic fatigue disease is selected from the group consisting of chronic cancer-related fatigue (CRF) and chronic fatigue syndrome (CFS). Hence, the present application in one embodiment relates to a method for diagnosis of CFS, comprising the step of determining the presence or absence of antibodies directed against one or more β-adrenergic receptors in a sample of the subject to be diagnosed, wherein the presence of antibodies directed against one or more β-adrenergic receptors is indicative of the presence of CFS in said subject. In a further embodiment the present application relates to a method for diagnosis of CRF, comprising the step of determining the presence or absence of antibodies directed against one or more β-adrenergic receptors in a sample of the subject to be diagnosed, wherein the presence of antibodies directed against one or more β-adrenergic receptors is indicative of the presence of CRF in said subject.

In some instances levels may be determined and compared to control levels, as further outlined herein below. Hence, the invention further pertains to a method for diagnosis of CFS comprising determining the level of antibodies directed against one or more β-adrenergic receptors in a sample of a subject to be diagnosed, wherein a level of antibodies directed against β-adrenergic receptors in the sample of the patient to be diagnosed higher than a control level is indicative of the presence or the risk of suffering from CFS, preferably levels of higher than 1.5 fold, 1.6 fold, 1.7 fold, 1.8 fold and most preferred 1.9 fold as compared to a control level derived from one or more subjects not having CFS is indicative of the presence of CFS in the subject to be diagnosed.

The skilled person is able to apply common standards in laboratory diagnosis to the present invention. In a preferred embodiment a determined level in said subject to be diagnosed above the $80^{th}$ percentile of the control levels is attributed to the presence of the antibody in the sample. Consequently, a determined level in said subject to be diagnosed above the $80^{th}$ percentile of the control levels is attributed to the presence a chronic fatigue disease in said subject. For example in a preferred embodiment a determined level in said subject to be diagnosed above the $80^{th}$ percentile of the control levels is attributed to the presence CFS in said subject. Further, a determined level in said subject to be diagnosed above the $80^{th}$ percentile of the control levels is attributed to the presence CRF in said subject. As will be outlined in greater detail herein below, even increased percentile values may be applied as the cut off. Hence, in one embodiment a determined level in said subject to be diagnosed above the $90^{th}$ percentile of the control levels is attributed to the presence of the antibody in the sample. Consequently, a determined level in said subject to be diagnosed above the $90^{th}$ percentile of the control levels is attributed to the presence a chronic fatigue disease in said subject. For example, in a preferred embodiment a determined level in said subject to be diagnosed above the 90$^{th}$ percentile of the control levels is attributed to the presence CFS in said subject. Further, in one embodiment a determined level in said subject to be diagnosed above the 90$^{th}$ percentile of the control levels is attributed to the presence CRF in said subject. In a preferred embodiment a determined level in said subject to be diagnosed above the 95$^{th}$ percentile of the control levels is attributed to the presence of the antibody in the sample. Consequently, in a preferred embodiment a determined level in said subject to be diagnosed above the 95$^{th}$ percentile of the control levels is attributed to the presence CFS in said subject. Further, in one embodiment a determined level in said subject to be diagnosed above the 95$^{th}$ percentile of the control levels is attributed to the presence CRF in said subject. Even higher cut-off values may be applied. The control levels may be derived from a population of subjects not having CFS, preferably from healthy a healthy population or a population of subjects suffering from a depression, more preferably from a healthy population.

The levels of antibodies directed against β-adrenergic receptors may also be compared to previously fixed values, e.g. standardized units. One approach to fix such units is outlined herein in greater detail. According to one embodiment, the invention also pertains to a method for diagnosis of a chronic fatigue disease, wherein the level of antibodies directed against one or more β-adrenergic receptors is determined in a sample from a subject to be diagnosed and wherein a level of anti-β1-adrenergic receptors antibodies above 10 units/ml is indicative of a chronic fatigue disease, preferably above 15 units/ml, more preferably above 18, further preferred above 20 units/ml; and/or wherein a level of anti-β2-adrenergic receptors antibodies above 5 units/ml is indicative of a chronic fatigue disease, preferably above 7 units/ml, more preferably above 9, further preferred above 10 units/ml. Preferred chronic fatigue diseases are CFS and CRF. Hence, according to one embodiment, the invention also pertains to a method for diagnosis of CFS, wherein the level of antibodies directed against one or more β-adrenergic receptors is determined in a sample from a subject to be diagnosed and wherein a level of anti-β1-adrenergic receptors antibodies above 10 units/ml is indicative of CFS, preferably above 15 units/ml, more preferably above 18, further preferred above 20 units/ml; and/or wherein a level of anti-β2-adrenergic receptors antibodies above κ units/ml is indicative of CFS, preferably above 7 units/ml, more preferably above 9, further preferred above 10 units/ml. According to a further embodiment the invention also pertains to a method for diagnosis of CRF, wherein the level of antibodies directed against one or more β-adrenergic receptors is determined in a sample from a subject to be diagnosed and wherein a level of anti-β1-adrenergic receptors antibodies above 10 units/ml is indicative of CRF, preferably above 15 units/ml, more preferably above 18, further preferred above 20 units/ml; and/or wherein a level of anti-β2-adrenergic receptors antibodies above 5 units/ml is indicative of CRF, preferably above 7 units/ml, more preferably above 9, further preferred above 10 units/ml.

The invention furthermore relates to the use of a β-adrenergic receptor or an antigenic peptide fragment thereof for the diagnosis of a chronic fatigue disease, preferably selected from CFS and CRF. Hence, the invention furthermore relates to the use of a β-adrenergic receptor or an antigenic peptide fragment thereof for the diagnosis CFS. Further, the invention relates to the use of a β-adrenergic receptor or an antigenic peptide fragment thereof for the diagnosis of CRF The present invention further relates to research and/or diagnostic kit for the diagnosis of a chronic fatigue disease, preferably selected from CFS and CRF, wherein the kit comprises a β-adrenergic receptor or an antigenic (immunogenic) peptide fragment thereof. Hence, the present invention relates to research and/or diagnostic kit for the diagnosis of CFS, wherein the kit comprises a β-adrenergic receptor or an antigenic (immunogenic) peptide fragment thereof. Further, the present invention relates to research and/or diagnostic kit for the diagnosis of CRF, wherein the kit comprises a β-adrenergic receptor or an antigenic (immunogenic) peptide fragment thereof.

The invention also relates to a method for the removal of β-adrenergic receptor antibodies from isolated blood, comprising the steps of:

(i) determining in a sample of a subject the presence or absence of an β-adrenergic receptor antibodies is determined in a sample; and (ii) removing β-adrenergic receptor antibodies from isolated blood of the subject.

DETAILED DESCRIPTION OF A PREFERRED EMBODIMENT

Figure 1:
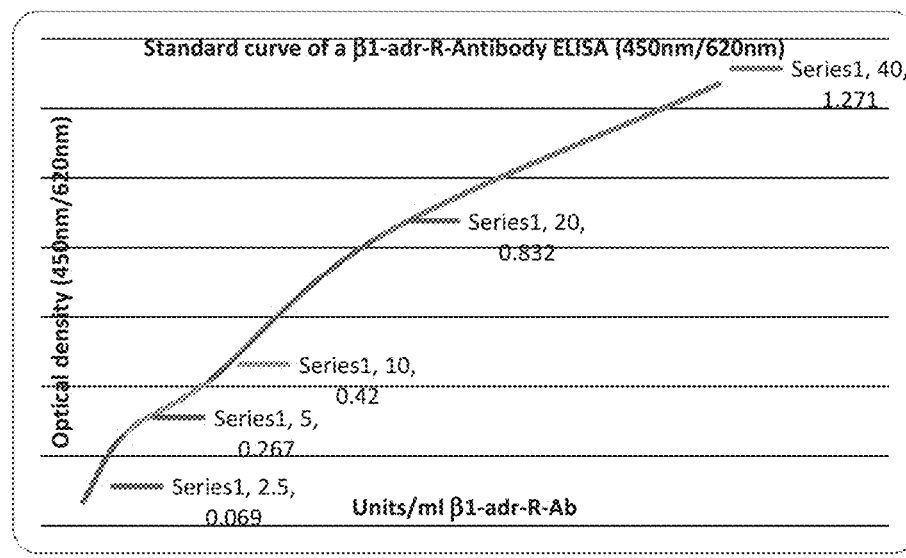
FIG. 1: Standard curve of β1-adrenergic receptors autoantibody ELISA. For details see Example 1.

The present invention is based on the surprising finding that in samples of patients suffering from CFS autoantibodies directed against β-adrenergic receptors can be detected. In other words the inventors have found that patients with CFS have a higher level of antibodies directed against β-adrenergic receptors in the blood as control groups suffering from depression or being reported as healthy. The invention is further based on the surprising finding that said autoantibodies are also present in another chronic fatigue disease, i.e. CRF. Hence, the inventors have for the first time provided evidence for patients with a chronic fatigue disease having a higher level of antibodies directed against β-adrenergic receptors in the blood as control groups suffering from depression or being reported as healthy.

The present invention is, hence, based on the finding of that levels of auto-antibodies directed against β-adrenergic receptors in subjects have diagnostic properties. The antibodies to be detected in connection with the present invention are therefore autoantibodies, i.e. those produced by immune system of the subject to be diagnosed or being or to be treated.

Determination of the presence of said antibodies may also be conducted via determining the level of antibodies directed against β-adrenergic receptors. If the level of antibodies is above a certain threshold, presence of antibody is given. Such threshold may be dependent on the actual assay used. In a preferred embodiment presence is attributed to a level which is significantly higher than the background (noise) of the used assay. In a further embodiment of the diagnostic method, the presence is determined through the comparison of the level of antibodies directed against β-adrenergic receptors in the sample of the subject to be diagnosed to a control level.

Such control level may for example be the level obtained in samples of subjects not having a chronic fatigue disease, like CRF or CFS, preferably not having CFS, more preferably from healthy subjects or subjects suffering from a depression. In one embodiment of the present invention determining the presence or absence of antibodies directed against one or more β-adrenergic receptor comprises the steps of (i) determining the level of antibodies directed against one or more β-adrenergic receptor in a sample from a subject to be diagnosed, and (ii) comparing the determined level in the sample to a control level of antibodies directed against one or more β-adrenergic receptor derived from subjects without a chronic fatigue disease, like CRF or CFS, preferably without CFS wherein an increased level in the sample from the subject to be diagnosed as compared to the control level is attributed to the presence of antibodies directed against one or more β-adrenergic receptor in the subject to be diagnosed, and wherein a level equal or decreased level in the sample from the subject to be diagnosed as compared to the control level is attributed to the absence of antibodies directed one or more β-adrenergic receptor.

In one specific embodiment the β-adrenergic receptor is preferably a β1-adrenergic receptor. In this embodiment the invention relates to a method for diagnosis of a chronic fatigue disease, like CRF or CFS, preferably CFS, comprising the step of determining the presence or absence of antibodies directed against β1-adrenergic receptor in a sample of the subject to be diagnosed, wherein the presence of antibodies directed against β1-adrenergic receptors is indicative of the presence or the risk of developing a chronic fatigue disease, like CRF or CFS, preferably CFS, respectively, in said subject. In one embodiment of the present invention determining the presence or absence of antibodies directed against β1-adrenergic receptor comprises the steps of (i) determining the level of antibodies directed against β1-adrenergic receptor in a sample from a subject to be diagnosed, and (ii) comparing the determined level in the sample to a control level of antibodies directed against β1-adrenergic receptor derived from subjects without a chronic fatigue disease, like CRF or CFS, preferably without CFS; wherein an increased level in the sample from the subject to be diagnosed as compared to the control level is attributed to the presence of antibodies directed against β1-adrenergic receptor in the subject to be diagnosed, and wherein a level equal or decreased level in the sample from the subject to be diagnosed as compared to the control level is attributed to the absence of antibodies directed β1-adrenergic receptor.

In one specific embodiment the β-adrenergic receptor is preferably a β2-adrenergic receptor. In this embodiment the invention relates to a method for diagnosis of a chronic fatigue disease, like CRF or CFS, preferably CFS, comprising the step of determining the presence or absence of antibodies directed against β2-adrenergic receptors in a sample of the subject to be diagnosed, wherein the presence of antibodies directed against β2-adrenergic receptor is indicative of the presence or the risk of developing a chronic fatigue disease, like CRF or CFS, preferably CFS, respectively, in said subject. In one embodiment of the present invention determining the presence or absence of antibodies directed against β2-adrenergic receptor comprises the steps of (i) determining the level of antibodies directed against β2-adrenergic receptor in a sample from a subject to be diagnosed, and (ii) comparing the determined level in the sample to a control level of antibodies directed against β2-adrenergic receptor derived from subjects without a chronic fatigue disease, like CRF or CFS, preferably without CFS; wherein an increased level in the sample from the subject to be diagnosed as compared to the control level is attributed to the presence of antibodies directed against β2-adrenergic receptor in the subject to be diagnosed, and wherein a level equal or decreased level in the sample from the subject to be diagnosed as compared to the control level is attributed to the absence of antibodies directed β2-adrenergic receptor.

The diagnostic output of the method according to the present invention may be further improved if the presence of antibodies against more than one β-adrenergic receptor is determined. In such embodiment the invention relates to method for diagnosis of a chronic fatigue disease, like CRF or CFS, preferably CFS, comprising the step of determining the presence or absence of antibodies directed against two or more β-adrenergic receptors, preferably directed against β1-adrenergic receptor and β2-adrenergic receptor, in a sample of the subject to be diagnosed, wherein the presence of antibodies directed against two or more β-adrenergic receptors is indicative of the presence or the risk of developing a chronic fatigue disease, like CRF or CFS, preferably CFS, respectively, in said subject. The invention also relates to a method for diagnosis of a chronic fatigue disease, like CRF or CFS, preferably CFS, comprising the step of determining the presence or absence of antibodies directed against β1-adrenergic receptor and/or β2-adrenergic receptor, in a sample of the subject to be diagnosed, wherein the presence of antibodies directed against β1-adrenergic receptor and/or β2-adrenergic receptor is indicative of the presence or the risk of developing a chronic fatigue disease, like CRF or CFS, preferably CFS, respectively, in said subject. In a particular preferred embodiment, the invention also relates to a method for diagnosis of a chronic fatigue disease, like CRF or CFS, preferably CFS, comprising the step of determining the presence or absence of antibodies directed against β1-adrenergic receptor and β2-adrenergic receptor, in a sample of the subject to be diagnosed, wherein the presence of antibodies directed against β1-adrenergic receptor and/or antibodies directed against β2-adrenergic receptor is indicative of the presence or the risk of developing a chronic fatigue disease, like CRF or CFS, preferably CFS, respectively, in said subject.

The skilled person will also understand that the "control" level may be implicated in the used assay for detecting said autoantibodies. The skilled person hence may chose particulars of the assay so that the test is positive for the presence of the antibody in the sample if levels above a certain level is reached and vice versa be negative for the presence of said autoantibody if levels are determined that are below the control value. The control level is preferably derived from a subject not having a chronic fatigue disease, like CRF or CFS, preferably CFS, respectively, more preferably from a healthy subject or a subject suffering from depression.

The term "chronic fatigue disease" relates to a disease with persistent fatigue that does not relieved by rest. Preferably "chronic" in this context refers to the disease being present in the subject for at least 6 months, more preferably at least 12 months. "chronic fatigue disease" in context with the present invention preferably relates to disorder in a subject, wherein the subject exhibits at least 6 of the following symptoms over a period of at least 12 months: 1) distinct fatigue, energy loss, or inappropriately increased need for rest affecting daily life; 2) sense of generic weakness or heaviness in one's limbs; 3) concentration disorders; 4) disorder of the short-term memory; 5) disturbed sleep pattern (insomnia or undue need of sleep); 6) unrelaxing sleep; 7) lack of motivation or interest for normal activities of daily routine; 8) the feeling of the need to constrain oneself for every activity; 9) difficulties in the accomplishment of everyday's life; 10) malaise for several hours following on physical exercise; 11) distinct emotional reactions on the felt fatigue (e.g. depressiveness, frustration, testiness).

Until today two major groups of chronic fatigue diseases are known, i.e. CRF and CFS. The present data now demonstrate that it is possible to diagnose (and to prognose) chronic fatigue diseases using the method according to the present invention. In a preferred embodiment the chronic fatigue disease according to the present invention is a autoimmune driven chronic fatigue disease. More preferred the chronic fatigue disease according to the present invention is selected from the group consisting of CFS and CRF. In a further embodiment, CFS and CRF according to the invention are autoimmune driven CFS and CRF, respectively. Particularly preferred the chronic fatigue disease is CFS.

"Chronic cancer-related fatigue" (CRF) in context with the present invention relates to a cancer-related fatigue which is chronic, i.e. the disease being present in the subject for at least 6 months, more preferably at least 12 months. A cancer-related fatigue in context of the invention is a fatigue that occurs as a symptom associated with cancer and/or cancer treatment, preferably as defined by the National Comprhensive Cancer Network, i.e. it is preferably a distressing persistent, subjective sense of physical, emotional and/or cognitive tiredness or exhaustion related to cancer or cancer treatment that is not proportional to recent activity and interferes with usual functioning. Chronic cancer related fatigue (CRF) is preferably according to the ICD-10 criteria. In a preferred embodiment a chronic cancer related fatigue is a chronic fatigue in a subject suffering from cancer or undergoing a cancer treatment or had been undergone cancer treatment at that shows at least 6 of the following 11 symptoms are present in the patient (see Cella D, et al., J Clin Oncol (2001)): 1) distinct fatigue, energy loss, or inappropriately increased need for rest affecting daily life; 2) sense of generic weakness or heaviness in one's limbs; 3) concentration disorders; 4) disorder of the short-term memory; 5) disturbed sleep pattern (insomnia or undue need of sleep); 6) unrelaxing sleep; 7) lack of motivation or interest for normal activities of daily routine; 8) the feeling of the need to constrain oneself for every activity; 9) difficulties in the accomplishment of everyday's life; 10) malaise for several hours following on physical exercise; 11) distinct emotional reactions on the felt fatigue (e.g. depressiveness, frustration, testiness). Most of the patients undergoing tumor/cancer therapy suffer from fatigue during the treatment, e.g. 70 to 80% of tumor patients undergoing chemotherapy or radiation therapy suffer from tumor fatigue Even though fatigue disappears in most of the patients, about 30% of the patients retain fatigue for more than 12 months, i.e. are suffering from a chronic cancer-related fatigue (CRF; Bower J E, Cancer-related fatigue-mechanisms, risk factors, and treatments. Nat Rev Clin Oncol. 2014 October; 11:597-609).

The term "chronic fatigue syndrome" (CFS) is also referred to as systemic exertion intolerance disease (SEID), myalgic encephalomyelitis (ME), post-viral fatigue syndrome (PVFS), chronic fatigue immune dysfunction syndrome (CFIDS) defined by ICD-10 as G93.3 ([[http://]]apps.who.int/classifications/icd10/browse/2015/en#/G93.3); by ICD-9 as 780.71 ([[http://]](www.icd9data.com/2015/Volume1/780-799/780-789/780/780.71.htm). Accordingly, it may be defined as a condition lasting for more than 6 months in which a person feels tired most of the time and may have trouble concentrating and carrying out daily activities. Other symptoms include sore throat, fever, muscle weakness, headache, and joint pain. Furthermore, it is defined as a syndrome characterized by persistent or recurrent fatigue, diffuse musculoskeletal pain, sleep disturbances, and subjective cognitive impairment of 6 months duration or longer. Symptoms are not caused by ongoing exertion; are not relieved by rest; and result in a substantial reduction of previous levels of occupational, educational, social, or personal activities. Minor alterations of immune, neuroendocrine, and autonomic function may be associated with this syndrome. There is also considerable overlap between this condition and fibromyalgia. (from Semin Neurol 1998; 18(2):237-242; Ann Intern Med 1994; 15; 121(12): 953-959). CFS is a clinical diagnosis characterized by an unexplained persistent or relapsing chronic fatigue that is of at least six months' duration, is not the result of ongoing exertion, is not substantially alleviated by rest, and results in substantial reduction of previous levels of occupational, educational, social, or personal activities. Common concurrent symptoms of at least six months duration include impairment of memory or concentration, diffuse pain, sore throat, tender lymph nodes, headaches of a new type, pattern, or severity, and nonrestorative sleep. The etiology of CFS may be viral or immunologic. Fibromyalgia may represent related disorder. CFS is also known as myalgic encephalomyelitis. CFS is a disorder that causes extreme fatigue. This fatigue is not the kind of tired feeling that goes away after you rest. Instead, it lasts a long time and limits your ability to do ordinary daily activities. Symptoms of CFS include fatigue for 6 months or more and experiencing other problems such as muscle pain, memory problems, headaches, pain in multiple joints, sleep problems, sore throat and tender lymph nodes. The CFS may also be characterized by chronic fatigue, mild fever, lymphadenopathy, headache, myalgia, arthralgia, depression, and memory loss; candidate etiologic agents include epstein-barr and other herpesviruses. In a preferred embodiment CFS refers to a syndrome where any of the above mentioned symptoms rest for more than 6 months. Furthermore, CFS refers to a syndrome initiated by a viral infection, preferably by an infection with EBV. CFS, hence, is a definition for a heterogenic group of diseases.

"Diagnosis" in context with the present invention preferably denotes the assessment of a disease status of a subject. In one embodiment it also refers to risk stratification, prognosis, monitoring, or therapy control. In the present invention, the term risk stratification denotes a statistical process by which the quality of a certain form of treatment can be assessed independently of patient case-mix. Preferably diagnosis refers to diagnosis. Thus, the quality of a certain form of treatment for a given medical condition may generally be assessed independently of certain risk factors which influence the outcome of said treatment, such as for example, the subject's sex, age, ethnic background, genetic predispositions, prior history of diseases and the like. Equally, the assessment may be made for certain sub-groups of subjects, e.g. of a certain age, in order to assess the quality of a certain form of treatment for said sub-group. In the present invention, the term prognosis denotes a prediction of how a subject's (e.g. a patient's) medical condition will progress. This may include an estimation of the chance of recovery or the chance of an adverse outcome for said subject. In the present invention, the term monitoring denotes the observation of the state or progression of a subject's medical condition by measuring the level of a certain diagnostic marker or markers for said medical condition at various points of time. In the present invention, the term therapy control denotes the attribution of a certain form of treatment, such as the administration of a medicament or antibody removal, to the state or progression of a subject's medical condition by measuring the level of a certain diagnostic marker or markers for said medical condition at various points of time, preferably before and after the treatment. In this way, it may be determined whether said treatment is adequate to treat said medical condition, or whether the therapy will have to be adjusted, e.g. by altering the dosage of the medicament, or will have to be replaced by another form of treatment, e.g. another medicament.

The skilled person will however, acknowledge that the inventors for the first time present a diagnostic marker that can reliably diagnose a chronic fatigue disease, like CFS or CRF in a subject. He will also acknowledge this in front of the background that a chronic fatigue disease, like CFS or CRF is a heterogeneous diagnosis, for which now a subgroup could be identified, i.e. the subgroup of a chronic fatigue disease, like CFS or CRF patients showing presence of antibodies directed against a β-adrenergic receptor. Hence, the diagnostic method as disclosed herein is in a preferred embodiment a method for determining whether a subject suspected to have a chronic fatigue disease, like CFS or CRF, preferably CFS belongs to the subgroup of chronic fatigue disease patients, like CFS or CRF patients, preferably CFS patients, respectively, showing presence of antibodies directed against a β-adrenergic receptor, wherein upon determination of the presence or increased levels of a β-adrenergic receptor antibody the subject is grouped into the subgroup of subject having chronic fatigue disease, like CFS or CRF, preferably CFS, respectively, conveyed by presence or increased levels of a β-adrenergic receptor antibody. Furthermore, the diagnostic method as disclosed herein in one embodiment is a method for characterizing chronic fatigue disease, like CFS or CRF, preferably CFS, in a subject, wherein upon determination of the presence or increased levels of a β-adrenergic receptor antibody the chronic fatigue disease, like CFS or CRF, preferably CFS, respectively, in a subject is characterized as the subgroup of a chronic fatigue disease, like CFS or CRF, preferably CFS, respectively, conveyed by presence or increased levels of a β-adrenergic receptor antibody. In a preferred embodiment the method according to the present invention is a method for diagnosing a chronic fatigue disease, like CFS or CRF, preferably CFS, respectively, in a subgroup of subjects suffering from a chronic fatigue disease, like CFS or CRF, preferably CFS, respectively. In other words the invention also relates to a method for identifying a subgroup of subjects having a chronic fatigue disease, like CFS or CRF, preferably CFS, respectively, the subgroup preferably showing the presence of antibodies directed against β-adrenergic receptors as outlined herein, preferably directed against β1-adrenergic receptor or directed against β2-adrenergic receptor.

The skilled person is aware that he also may have to consider further parameters to diagnose the subject. In the context of the present invention the subject to be diagnosed is a mammal, preferably a human. The subject is preferably a human suspected to have a chronic fatigue disease, like CFS or CRF, preferably CFS. The diagnosis to be performed may be dependent on said further parameters. For example a certain patient may have symptoms usually associated with a chronic fatigue disease, like CFS or CRF, preferably CFS as outlined herein above. However, as symptoms often may be associated with different diseases, specificity may not be high enough. Hence, the skilled person will instantly appreciate the provision of the method according to the present invention which allows to diagnose a chronic fatigue disease, like CFS or CRF, preferably CFS, and furthermore to specify symptom-based diagnosis.

The antibodies to be detected or determined according to the present invention are directed against a β-adrenergic receptor. This means that the antibodies specifically bind a β-adrenergic receptor. β-adrenergic receptors are known by the skilled person and include β1-adrenergic receptor, β2-adrenergic receptor, and β3-adrenergic receptor. The adrenergic receptors (or adrenoceptors) are a class of G protein-coupled receptors that are targets of the catecholamines, especially norepinephrine (noradrenaline) and epinephrine (adrenaline). Many cells possess these receptors, and the binding of a catecholamine to the receptor will generally stimulate the sympathetic nervous system. The sympathetic nervous system is responsible for the fight-or-flight response, which includes widening the pupils of the eye, mobilizing energy, and diverting blood flow from non-essential organs to skeletal muscle. There are two main groups of adrenergic receptors, α and β, with several subtypes. α-adrenergic receptors have the subtypes α1 (a Gq coupled receptor) and α2 (a Gi coupled receptor). Phenylephrine is a selective agonist of the α receptor. β-adrenergic receptors have the subtypes β1, β2 and β3. All three are linked to Gs proteins (although β2 also couples to Gi), which in turn are linked to adenylate cyclase. Agonist binding thus causes a rise in the intracellular concentration of the second messenger cAMP. Downstream effectors of cAMP include cAMP-dependent protein kinase (PKA), which mediates some of the intracellular events following hormone binding. Isoprenaline is a non-selective agonist. The antibodies to be determined in the method according to the present invention are preferably directed against β1-adrenergic receptor and/or β2-adrenergic receptor, i.e. the antibodies specifically bind them. Specific binding of an antibody normally occurs via binding of a binding site of the antigen. The antibodies of the present invention are those specifically binding to a β-adrenergic receptor or immunogenic fragments thereof. This binding may occur via recognition of sequence or structural epitopes. The skilled person is aware of methods of how to determine specific epitopes, e.g. fragments of the antigen β-adrenergic receptor, which are recognized and specifically bound by the antibodies to be determined. Fragments of a β-adrenergic receptor binding to the auto antibodies are called immunogenic or antigenic fragments. The terms "immunogenic" and "antigenic" are used interchangeably herein. Methods for determining fragments of an antigen binding the antibody are described in several publications which are incorporated herein by reference (see e.g. Gershoni, J M; Roitburd-Berman, A; Siman-Tov, D D; Tarnovitski Freund, N; Weiss, Y (2007). "Epitope mapping: The first step in developing epitope-based vaccines". BioDrugs 21 (3): 145-56; Westwood, M R; Hay, F C (2001). Epitope Mapping: a practical approach. Oxford, Oxfordshire: Oxford University Press. ISBN 0-19-963652-4; Flanagan et al. (2011), "Mapping Epitopes with H/D-Ex Mass Spec". Genetic Engineering and Biotechnology news; 31(1); Gaseitsiwe, S.; Valentini, D.; Mandavifar, S.; Reilly, M.; Ehrnst, A.; Maeurer, M. (2009) "Peptide Microarray-Based Identification of *Mycobacterium tuberculosis* Epitope Binding to HLA-DRB1*0101, DRB1*1501, and DRB1*0401". Clinical and Vaccine Immunology 17 (1): 168-75; Linnebacher, Michael; Lorenz, Peter; Koy, Cornelia; Jahnke, Annika; Born, Nadine; Steinbeck, Felix; Wollbold, Johannes; Latzkow, Tobias et al. (2012). "Clonality characterization of natural epitope-specific antibodies against the tumor-related antigen topoisomerase IIa by peptide chip and proteome analysis: A pilot study with colorectal carcinoma patient samples" Analytical and Bioanalytical Chemistry 403 (1): 227-38; Cragg, M. S. (2011). "CD20 antibodies: Doing the time warp". Blood 118 (2): 219-20; Banik, Soma S. R.; Doranz, Benjamin J (2010). "Mapping Complex Antibody Epitopes". Genetic Engineering and Biotechnology News 3 (2): 25-8; and Paes, Cheryl; Ingalls, Jada; Kampani, Karan; Sulli, Chidananda; Kakkar, Esha; Murray, Meredith; Kotelnikov, Valery; Greene, Tiffani A. et al. (2009). "Atomic Level Mapping of Antibody Epitopes on a GPCR". Journal of the American Chemical Society 131 (20): 6952-4). In context with the present invention β-adrenergic receptor antibodies are understood as any immunoglobulin specifically recognizing/binding to a β-adrenergic receptor, preferably selected from the group consisting of β1-adrenergic receptor, β2-adrenergic receptor and β3-adrenergic receptors, particularly preferred selected from the group consisting of β1-adrenergic receptor, and β2-adrenergic receptor. The antibody to be detected in a some embodiments binds β1-adrenergic receptor, in this case the antibody preferably specifically binds a sequence comprising or consisting of SEQ ID NO: 1. The antibody to be detected in a some embodiments binds β2-adrenergic receptor, in this case the antibody preferably specifically binds a sequence comprising or consisting of SEQ ID NO: 2.

In the context of the present invention the β-adrenergic receptor antibodies to be detected may particularly be selected from the group of IgA-antibody, IgG-antibody and IgM-antibody, preferably an IgG antibody, e.g. IgG1, IgG2, IgG3 and IgG4. Most preferred IgG antibodies directed against a β-adrenergic receptor, preferably β1-adrenergic receptor and/or β2-adrenergic receptor, are determined.

The control levels as disclosed herein refer to control levels of antibodies directed against a β-adrenergic receptor or an antigenic fragment thereof. It will be readily understood by the skilled person that the control levels from subjects having the desired disease or response as defined in the methods and to which the determined levels are compared to, are not necessarily determined in parallel but may be represented by previously determined levels. Nevertheless, control levels may be determined in parallel. The skilled person with the disclosure of the present invention and his knowledge is able to determine such levels, as outlined herein. Hence, the control levels of the present invention may be previously defined thresholds. Preferred thresholds are disclosed herein but may also be determined by the person of ordinary skills in the art when considering the disclosure of the present application. Furthermore, it will be acknowledged by the skilled person that control levels are, like the levels to be determined in the subject to be diagnosed, determined in samples of the recited subjects having the desired disease or being healthy, i.e. not having the recited disease. Preferably, the sample is the same kind of sample as the sample of the person to be diagnosed, e.g. when the sample of the latter is serum, the control levels are preferably determined in serum samples derived from the control subjects.

As outlined herein, the levels of antibodies directed against β-adrenergic receptor in a sample of the patient to be diagnosed may be compared to the control groups as defined herein. However, in one embodiment the levels are compared to fixed values, i.e. thresholds under or over which a certain diagnosis, or prognosis is given. To this end, unit-standards may be applied. The present inventors set out such standard for the β-adrenergic receptor antibodies using one armed serum samples from systemic sclerosis patients. The inventors took a serum sample of a systemic sclerosis patient. However, it will be acknowledged by the skilled person that also other samples may be taken to set a different standard, e.g. samples of patients, as long as antibodies directed against the desired β-adrenergic receptor are present in an amount sufficient to allow preparation of a standard curve. Nevertheless the principle of generating a standard (units) is the same in any case and is exemplified herein using serum samples of systemic sclerosis patients. In the context of the present invention "units/ml", unless specified otherwise, refers to the concentration of antibodies standardized as exemplified herein. The application of the standard may be dependent on the actual target of the antibody.

Hence, in the embodiments relating to detection of β1-adrenergic receptor antibodies of the present invention 40 units/ml refers to a dilution of 1:800 of a serum sample of systemic sclerosis patients. The serum sample may be derived from a single patient or of a cohort of a plurality of patients, e.g. a cohort of 200 patients suffering from systemic sclerosis. In one preferred embodiment the standard for the concentrations of the autoimmune antibodies is generated in the following way: a serum sample of a systemic sclerosis patient (or a larger cohort) is diluted (a) 1:800 for standard point 40 Units/ml, (b) 1:3200 for standard point 20 Units/ml, (c) 1:12800 for standard point 10 Units/ml, (d) 1:25600 for standard point 5 Units/ml, and (e) 1:102400 for standard point 2.5 Units/ml.

Hence, in the embodiments relating to the detection of β2-adrenergic receptor antibodies of the present invention 40 units/ml refers to a dilution of 1:4000 of a serum sample of systemic sclerosis patients. The serum sample may be derived from a single patient or of a cohort of a plurality of patients, e.g. a cohort of 200 patients suffering from systemic sclerosis. In one preferred embodiment the standard for the concentrations of the autoimmune antibodies is generated in the following way: a serum sample of a systemic sclerosis patient (or a larger cohort) is diluted (a) 1:4000 for standard point 40 Units/ml, (b) 1:8000 for standard point 20 Units/ml, (c) 1:16000 for standard point 10 Units/ml, (d) 1:24000 for standard point 5 Units/ml, and (e) 1:84000 for standard point 2.5 Units/ml.

Figure 2:
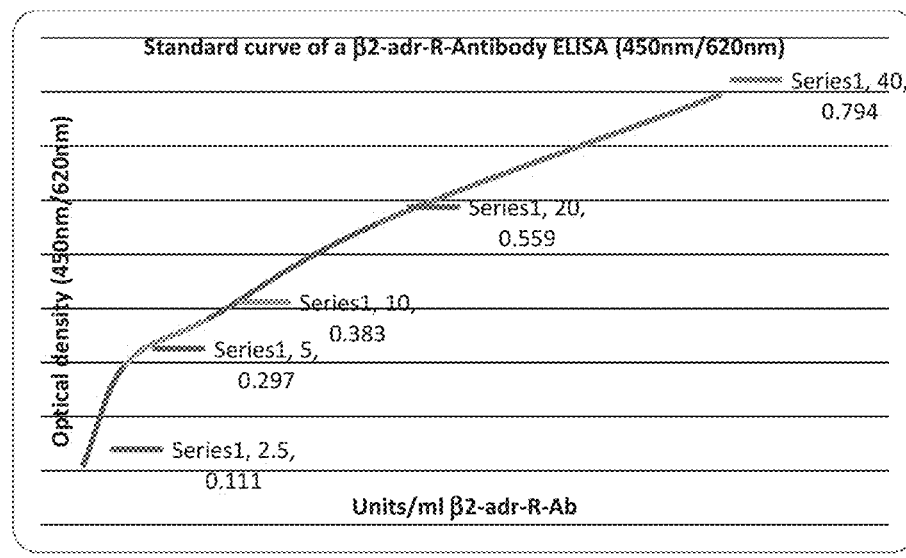
FIG. 2: Standard curve of β2-adrenergic receptors autoantibody ELISA. For details see Example 2.

These standards are then used for the immunoassay chosen, e.g. ELISA, and then correlated with the respective read-out value, e.g. for ELISA the ratio of optical density at 450 nm and optical density at 620 nm. A typical standard curve of β1-adrenergic receptor and β2-adrenergic receptor auto-antibody ELISA is shown in FIGS. 1 and 2, respectively. Nevertheless, the skilled person will readily understand that it may also be possible to standardize the levels of β-adrenergic receptor antibodies using different samples, e.g. samples of patients having other autoimmune diseases.

"Equal" level in context with the present invention means that the levels differ by not more than ±10%, preferably by not more than ±5%, more preferably by not more than ±2%. "Decreased" or "increased" level in the context of the present invention mean that the levels differ by more than 10%, preferably by more than 15%, preferably more than 20%.

Preferably herein, the sample is a sample of a bodily fluid or a tissue of the subject to be diagnosed. A bodily fluid sample is preferred. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, more preferably a serum sample or a plasma sample. Serum samples particularly preferred samples in the context of the present invention.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, and dialysis. Pre-treatments may also include the addition of chemical or biochemical substances to the solution, such as acids, bases, buffers, salts, solvents, reactive dyes, detergents, emulsifiers, chelators.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

"Serum" is the liquid fraction of whole blood that is collected after the blood is allowed to clot. When coagulated blood (clotted blood) is centrifuged serum can be obtained as supernatant. It does not contain fibrinogen, although some clotting factors remain.

In a further embodiment the methods according to the present invention may further comprise an initial step of providing a sample, e.g. of a bodily fluid, of a subject.

In the method of the present invention, the antibodies directed against a β-adrenergic receptor are preferably detected in an immunoassay. Suitable immunoassays may be selected from the group of immunoprecipitation, enzyme immunoassay (EIA), enzyme-linked immunosorbenassys (ELISA), radioimmunoassay (RIA), fluorescent immunoassay, a cytometric bead array (CBA), a chemiluminescent assay, an agglutination assay, nephelometric assay, turbidimetric assay, a Western Blot, a competitive immunoassay, a noncompetitive immunoassay, a homogeneous immunoassay a heterogeneous immunoassay, a bioassay and a reporter assay such as a luciferase assay. Preferably herein the immunoassay is an enzyme linked immunosorbent assay (ELISA).

In the context of the immunoassays of the present invention the "β-adrenergic receptor" may be present in its natural cellular environment and can be used together with the material associated with the receptor in its natural state as well as in isolated form with respect to its primary, secondary and tertiary structures. The receptor is well known to those skilled in the art. The protein or its immunogenic (antigenic) fragment is preferably used in isolated form, i.e. essentially free of other proteins, lipids, carbohydrates or other substances naturally associated with the β-adrenergic receptor, e.g. β1-adrenergic receptor or β2-adrenergic receptor. "Essentially free of" means that the protein or its immunogenic fragment is at least 75%, preferably at least 85%, more preferably at least 95% and especially preferably at least 99% free of other proteins, lipids, carbohydrates or other substances naturally associated with the β-adrenergic receptor.

In connection with the present invention, the naturally occurring protein as well as all modifications, mutants or derivatives of a β-adrenergic receptor, preferably β1-adrenergic receptor or β2-adrenergic receptor, can be used. This includes all naturally present modifications as known to the skilled person. Similarly, a β-adrenergic receptor produced by means of recombinant techniques, which includes amino acid modifications, such as inversions, deletions, insertions, additions etc. can be used according to the invention provided that this part of the essential function of the β-adrenergic receptor is present, namely the capability of binding antibodies. Such recombinant techniques include the expression of the β-adrenergic receptor in a host cell using an expression vector suited for the selected host cell. The skilled person is able to choose suited host cells and expression vector systems based on his common general knowledge. As the β-adrenergic receptor protein is a trans-membrane protein, membrane extracts of the host cells expressing the receptor can be produced and used as the antigen. One preferred host cell system are Chinese Hamster Ovary cells (CHO cells) with the appropriate expression vector. The β-adrenergic receptor being used may also comprise exceptional amino acids and/or modifications of such as alkylation, oxidation, thiol-modification, denaturation, oligomerization and the like. The β-adrenergic receptor can also be synthesized by chemical means. According to the invention the β-adrenergic receptor particularly can be a protein and/or peptide or a fusion protein, which in addition to other proteins, peptides or fragments thereof, includes the β-adrenergic receptor as a whole or in part. Using conventional methods, peptides or polypeptides of the β-adrenergic receptor which have functionally analogs, analogous properties can be determined by those skilled in the art. For example such polypeptides or peptides have 50-60%, 70% or 80%, preferably 90%, more preferably 95%, and most preferably 98% sequence homology to peptides identified as the β-adrenergic receptor, and said homology can be determined, e.g. by means of Smith-Waterman homology search algorithm, using the MPFRCH program (Oxford Molecular), for example. β-adrenergic receptor preferably refers to β1-adrenergic receptor or β2-adrenergic receptor, preferably having the sequence of SEQ ID NO:1 or SEQ ID NO:2, respectively.

The term "peptide" or "polypeptide" of a β-adrenergic receptor used in the present invention, comprises also molecules differing from the original sequence by deletion(s), insertion(s), substitution(s) and/or other modifications well known in the prior art and/or comprising a fragment of the original amino acid molecule, the β-adrenergic receptor still exhibiting the properties mentioned above. Such a peptide has preferably at least a length of 50 residues but may also be shorter, e.g. at least 12, 15, 20 or 25 amino acid residues in length. For example one or more of the extracellular loops may be used. Also included are allele variants and modifications. Methods of producing the above changes in the amino acid sequence are well known to those skilled in the art and have been described in the standard textbooks of molecular biology, e.g. Sambrook et al., supra. Those skilled in the art will also be able to determine whether to protein or a fragment of β-adrenergic receptor, thus, modified still has the properties mentioned above. The amino acid sequence of β-adrenergic receptor is known. Database entries exist in several well known Databases. When refereeing to the amino acid sequence of β-adrenergic receptor any amino acid sequence known is meant, particularly those disclosed in common databases, preferably of human origin, preferably β1-adrenergic receptor or β2-adrenergic receptor. β1-adrenergic receptor in humans is encoded by the ADRB1 gene (Entrez #153; "Entrez Gene: gene-centered information at NCBI", Nucleic Acids Res. Jan. 1, 2005; 33 (Database issue): D54-D58)). A preferred sequence of the β1-adrenergic receptor is given herein, i.e. SEQ ID NO: 1. The β2-adrenergic receptor in humans is encoded by the ADRB2 gene (Entrez #154; "Entrez Gene: gene-centered information at NCBI", Nucleic Acids Res. Jan. 1, 2005; 33 (Database issue): D54-D58)). A preferred sequence of the β2-adrenergic receptor is given herein, i.e. SEQ ID NO: 2.

The β-adrenergic receptor may be glycosylated in vivo. In the present specification all of the above illustrated modifications of a β-adrenergic receptor will be referred to as "functionally analogous peptides or proteins" in brief.

The immunoassays can be homogeneous or heterogeneous assays, competitive and non competitive assays. In a particularly preferred embodiment, the assay is in the form of a sandwich assay, which is a non-competitive immunoassay, wherein the antibodies directed against a β-adrenergic receptor (i.e. the "analyte") to be detected and/or quantified are allowed to bind to an immobilized β-adrenergic receptor protein (e.g. comprised in a membrane fraction of CHO cells as exemplified herein) or immunogenic peptide fragments thereof and to a secondary antibody. The β-adrenergic receptor or the immunogenic fragment thereof (i.e. a peptide), may e.g., be bound to a solid phase, e.g. a bead, a surface of a well or other container, a chip or a strip, and the secondary antibody is an antibody which is labeled, e.g. with a dye, with a radioisotope, or a reactive or catalytically active moiety such as a peroxidase, e.g. horseradish peroxidase. The amount of labeled antibody bound to the analyte is then measured by an appropriate method. The general composition and procedures involved with "sandwich assays" are well-established and known to the skilled person (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134, incorporated herein by reference). Sandwich immunoassays can for example be designed as one-step assays or as two-step assays.

The detectable label may for example be based on fluorescence or chemiluminescence. The labelling system comprises rare earth cryptates or rare earth chelates in combination with a fluorescence dye or chemiluminescence dye, in particular a dye of the cyanine type. In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk Othmer, Encyclopedia of chemical technology, 4th ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

The "sensitivity" of an assay relates to the proportion of actual positives which are correctly identified as such, i.e. the ability to identify positive results (true positives positive results/number of positives). Hence, the lower the concentrations of the analyte that can be detected with an assay, the more sensitive the immunoassay is. The "specificity" of an assay relates to the proportion of negatives which are correctly identified as such, i.e. the ability to identify negative results (true negatives/negative results). For an antibody the "specificity" is defined as the ability of an individual antigen binding site to react with only one antigenic epitope. The binding behaviour of an antibody can also be characterized in terms of its "affinity" and its "avidity". The "affinity" of an antibody is a measure for the strength of the reaction between a single antigenic epitope and a single antigen binding site. The "avidity" of an antibody is a measure for the overall strength of binding between an antigen with many epitopes and multivalent antibodies.

An "immunogenic peptide" or "antigenic peptide" as used herein is a portion of the β-adrenergic receptor that is recognized (i.e., specifically bound) by the β-adrenergic receptor antibody. Such immunogenic peptides generally comprise at least 5 amino acid residues, more preferably at least 10, and still more preferably at least 20 amino acid residues of the receptor. However, they may also comprise at least 30, 40, 50, 60, 70, or 74 amino acid residues.

For the purposes of the immunoassays and diagnostic methods of the invention the β-adrenergic receptor can be produced by expression in cells, preferably eukaryotic cells or in cell free, preferably eukaryotic cell free systems. Hence, in the assays and methods of the invention the β-adrenergic receptor may be present in its natural cellular environment and can be used together with the material associated with the protein in its natural state as well as in isolated form. Suitable expression systems include Chinese hamster ovary (CHO) cells overexpressing the human β-adrenergic receptor. Hence, cell extracts (particularly extracts from CHO cells overexpressing the human β-adrenergic receptor) can be used to detect anti-β-adrenergic receptor antibodies. As β-adrenergic receptor is membrane bound the cell extract is preferably a membrane extract. Based on the weight of the whole protein or its immunogenic fragment in the preparation (e.g. the "extract") to be used according to the invention, the isolated protein should account for at least 0.5%, preferably at least 5% more preferably at least 25%, and in a particular preferred embodiment at least 50%. The protein may be used in isolated form, i.e. essentially free of other proteins, lipids, carbohydrates or other substances naturally associated with the receptor. "Essentially free of" means that the protein is at least 75%, preferably at least 85%, more preferably at least 95% and especially preferably at least 99% free of other proteins, lipids, carbohydrates or other substances naturally associated with the protein.

In particular, the method of the present invention, preferably the determining step, comprises the steps of (a) contacting the sample with a β-adrenergic receptor or an antigenic peptide fragment thereof under conditions allowing for the formation of a complex between β-adrenergic receptor antibodies directed against β-adrenergic receptor (anti-β-adrenergic receptor antibodies) with β-adrenergic receptor or a peptide fragment thereof, (b) detecting the complex. The β-adrenergic receptor preferably being selected from the group consisting of β1-adrenergic receptor and β2-adrenergic receptor as defined herein.

The β-adrenergic receptor or the antigenic peptide fragment thereof may preferably be immobilized on a surface. The complex may for example be detected using a secondary antibody against the Fc portion of the anti-β-adrenergic receptor antibody to be detected/determined. When the anti-β-adrenergic receptor antibody is an IgG-antibody, the secondary antibody may be an anti-IgG-antibody. Hence, in one embodiment the anti-β-adrenergic receptor antibody to be detected is an IgG-antibody and the secondary antibody is an anti-IgG-antibody, particularly preferred the subject is a human and the secondary antibody is an anti-human-IgG-antibody. The skilled person will understand that it is possible to detect total IgG, i.e. the method does not distinguish between the subtypes of IgG-antibodies. Hence, in one embodiment the secondary antibody is an anti human-total IgG-antibody. Nevertheless, in some embodiment it may be preferred that the subtypes are differentially detected. Hence, in a particular embodiment, the subject is a human and (i) the anti-β-adrenergic receptor is an IgG1-antibody and the secondary antibody is an anti-human-IgG1-antibody; or (ii) the anti-β-adrenergic receptor is an IgG2-antibody and the secondary antibody is an anti human-IgG2-antibody; or (iii) the anti-β-adrenergic receptor is an IgG3-antibody and the secondary antibody is an anti human-IgG3-antibody; or (iv) the anti-β-adrenergic receptor is an IgG4-antibody and the secondary antibody is an anti human-IgG4-antibody.

The secondary antibody may for example be labeled with a detectable marker, e.g. a peroxidase.

Furthermore, in the methods of the present invention further parameters of the subject may be considered as well for diagnosis, differential diagnosis, etc. Such parameters in a multivariate model may include gender, age, histological evaluation, and other biomarkers. A Cox-Proportional-Hazard regression predicts the dependent variable based on one or more independent variables. These predictors can either be measures (as e.g. level of a biomarker) or categorical data. The skilled person is aware of the fact that diagnostic markers only give a certain degree of sensitivity and specificity, as also outlined herein. He knows that different further parameters might be considered in order to increase both. Nevertheless, the present invention provides a new and superior marker for diagnosis, prognosis of an CFS as defined herein. In the context of the methods of the invention and particularly the immunoassays of the invention, the presence of one or more further diagnostic (bio)markers for the diseases is detected in the sample.

The term "biomarker" (biological marker) relates to measurable and quantifiable biological parameters (e.g., specific enzyme concentration, specific hormone concentration, specific gene phenotype distribution in a population, presence of biological substances) which serve as indices for health- and physiology-related assessments, such as disease risk, psychiatric disorders, environmental exposure and its effects, disease diagnosis, metabolic processes, substance abuse, cell line development, epidemiologic studies, etc. Furthermore, a biomarker is defined as a characteristic that is objectively measured and evaluated as an indicator of normal biological processes, or pathogenic processes. A biomarker may be measured on a biosample (as a blood, urine, or tissue test), it may be a recording obtained from a person (blood pressure, ECG, or Holter), or it may be an imaging test. Biomarkers can indicate a variety of health or disease characteristics, including the level or type of exposure to an environmental factor, genetic susceptibility, genetic responses to exposures, biomarkers of subclinical or clinical disease. Thus, a simplistic way to think of biomarkers is as indicators of disease trait (risk factor or risk biomarker), disease state (preclinical or clinical), or disease rate (progression). Accordingly, biomarkers can be classified as antecedent biomarkers (identifying the risk of developing an illness), screening biomarkers (screening for subclinical disease), diagnostic biomarkers (recognizing overt disease), staging biomarkers (categorizing disease severity), or prognostic biomarkers (predicting future disease course, including recurrence). Biomarkers may also serve as surrogate end points. The underlying principle is that alterations in the surrogate end point track closely with changes in the outcome of interest. Surrogate end points have the advantage that they may be gathered in a shorter time frame and with less expense than end points such as morbidity and mortality, which require large clinical trials for evaluation. Additional values of surrogate end points include the fact that they are closer to the exposure/intervention of interest and may be easier to relate causally than more distant clinical events. An important disadvantage of surrogate end points is that if clinical outcome of interest is influenced by numerous factors (in addition to the surrogate end point), residual confounding may reduce the validity of the surrogate end point. It has been suggested that the validity of a surrogate end point is greater if it can explain at least 50% of the effect of an exposure or intervention on the outcome of interest. For instance, a biomarker may be a protein (including antibodies), peptide or a nucleic acid molecule.

The invention also relates to the use of a β-adrenergic receptor or an antigenic peptide fragment thereof, preferably as set out herein above, for the diagnosis of a chronic fatigue disease, like CFS or CRF, preferably CFS. The β-adrenergic receptor preferably is β1-adrenergic receptor or β2-adrenergic receptor; preferably comprising or consisting of a sequence selected from the group consisting of SEQ ID NO: 1, and SEQ ID NO:2.

As will be apparent to the person skilled in the art, the "diagnostic" method may also being a prognostic method. For example the patho-mechanism of the disease may already being set on but no symptoms of the disease are yet present and/or detectable. Nevertheless, in such case the methods for diagnosis according to the present invention may be used to detect such "onset" of disease as a prognostic method, i.e. whether the subject will or has the risk to suffer from the disease in future. Hence, the term "method for diagnosis" and "method for prognosis" are to be used synonymously and can be exchanged herein were used.

In the context of the present invention, the levels of the anti-β-adrenergic receptor antibodies may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a diagnostic or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having CFS, or individuals having a depression but not CFS) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, below which the test is considered to be abnormal and above which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art; see e.g. Hanley et al. 1982. Radiology 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1 specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., disease) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of higher than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p-value; see, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Suitable threshold levels for the stratification of subjects into different groups (categories) can be determined for each particular combination of anti-β-adrenergic receptor antibodies, and disease. This can e.g. be done by grouping a reference population of patients according to their level of anti-β-adrenergic receptor antibodies into certain quantiles, e.g. quartiles, quintiles or even according to suitable percentiles. For each of the quantiles or groups above and below certain percentiles, hazard ratios can be calculated comparing the risk for an adverse outcome, e.g. a chronic fatigue disease, like CRF or CFS, e.g. in terms of disease rate, between those patients who have a certain disease and those who have not. In such a scenario, a hazard ratio (HR) above 1 indicates a higher risk for an adverse outcome for the patients. A HR below 1 indicates beneficial outcome. A HR around 1 (e.g. +/−0.1) indicates no elevated risk for the particular group of patients. By comparison of the HR between certain quantiles of patients with each other and with the HR of the overall population of patients, it is possible to identify those quantiles of patients who have an elevated risk and thereby stratify subjects according to the present invention.

In some cases presence of CFS will be detected in patients not showing presence β-adrenergic receptor antibodies (e.g. in the fifth quintile), while in other cases only patients with presence or increased levels of β-adrenergic receptor antibodies not have CFS (e.g. in the first quintile). However, with the above explanations, a skilled person is able to identify those groups of patients having CFS. In another embodiment of the invention, the diagnosis is determined by relating the patient's individual level of marker antibody to certain percentiles (e.g. 97.5th percentile) of a healthy population.

Kaplan-Meier estimators may be used for the assessment or prediction of the outcome or risk (e.g. diagnosis) of a patient.

The invention also pertains to a research and/or diagnostic kit for the diagnosis of CFS, wherein the kit comprises a β-adrenergic receptor or an antigenic peptide fragment thereof. The kit may further comprise means for detecting antibodies binding to said β-adrenergic receptor or antigenic peptide fragment thereof, e.g. an antibody directed to the Fc portion of the anti-β-adrenergic receptor antibodies to be detected, i.e. an anti-human-IgG-antibody. Embodiments of β-adrenergic receptor, antigenic peptide fragments thereof, the β-adrenergic receptor antibodies, the secondary antibodies as outlined herein above for the methods and immunoassays according to the present invention shall likewise apply for the kits according to the present invention. The β-adrenergic receptor is preferably selected from the group consisting of β1-adrenergic receptor and β2-adrenergic receptor. In a specific embodiment the β-adrenergic receptor comprises or consists of a sequence selected from the group consisting of SEQ ID NO: 1, and SEQ ID NO:2.

Such kits can comprise a carrier, package or container that is compartmentalized to receive one or more containers such as vials, tubes, and the like, each of the container(s) comprising one of the separate elements to be used in the method. The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non therapeutic application, and can also indicate directions for either in vivo or in vitro use, such as those described herein. Directions and/or other information can also be included on an insert which is included with the kit. The invention therefore relates to a kit for diagnosing CFS as outlined above, said kit comprising β-adrenergic receptor or an antigenic peptide thereof, and means to detect antibodies binding to said β-adrenergic receptor or peptide thereof. Preferably the kit is designed for a method of the present invention. It will be understood that the embodiments disclosed herein above β-adrenergic receptor or an antigenic peptide thereof as set out herein above also apply to the kit. The kit is designed to detect autoimmune antibodies in samples of subject and hence comprises means to detect such antibodies, particularly antibodies binding to said β-adrenergic receptor or peptide thereof. Such means are outlined herein above, e.g. for immunoassays. The embodiments set out for the immunoassays apply also to the kit of the invention. The kit of the present invention is meant for the detection of autoimmune antibodies in samples of subjects, e.g. blood. Hence, in one embodiment the kit comprise means for the preparation of blood, e.g. for gaining plasma or serum thereof. Furthermore, the kit may comprise control composition and/or standards. The control composition preferably comprises β-adrenergic receptor antibodies as positive control. Furthermore, the kit may comprise one or a plurality of standard compositions. A standard composition comprises β-adrenergic receptor antibodies at a defined concentration. As outlined herein, determination of concentration of autoimmune-antibodies may be performed using standard curves. These curves set out which concentration of antibodies in a sample or solution corresponds to what read-out value of the assay used, e.g. optical density or proportion of optical density at different wavelengths (e.g. 450 nm/620 nm). To this end the kits of the present invention may comprise one or more standard compositions having a defined concentration of β-adrenergic receptor antibodies, preferably of the kind to be detected in the method. A standard composition of the kits according to the present invention may for instance comprise β1-adrenergic receptor antibodies at concentrations selected from the group consisting of 40 units/ml, 20 units/ml, 10 units/ml, 5 units/ml, and 2.5 units/ml. A standard composition of the kits according to the present invention may for instance further or alternatively comprise β2-adrenergic receptor antibodies at concentrations selected from the group consisting of 40 units/ml, 20 units/ml, 10 units/ml, 5 units/ml, and 2.5 units/ml. The skilled person will acknowledge that it is possible—once a standard curve has been established for a certain range of values (e.g. 2.5 to 40 units/ml)—higher or lover values (e.g. 100 units/ml) may be extrapolated based on said standard curve. In one embodiment the kit comprises six standard compositions with the recited concentration. In another embodiment the kit comprises one standard composition with the highest concentration of the standard curve even higher, e.g. 100 units/ml or 40 units/ml for β1-adrenergic receptor antibodies and/or 40 units/ml for β1-adrenergic receptor antibodies, respectively. The other concentrations may be produced at the side of the end user by further dilutions using suited buffers, e.g. in PBS. A dilution buffer may therefore also be comprised in the kits according to the invention.

In common approach for treatment of autoimmune diseases is the isolation of auto-antibodies from the blood of the patient suffering from the disease. To this end, blood is isolated from the subject, the auto-antibodies are removed from the isolated blood, and the isolated blood is reinjected into the patient. Such approach is also known as plasmapheresis. As the inventors for the first time showed the correlation of the presence of auto-antibodies directed against β-adrenergic receptor antibodies with the presence of an autoimmune disease in a subject, it is apparently plausible to the skilled person that the removal of the antibodies from the blood of the patient will ameliorate the disease. Hence, the invention also relates to a method for the removal of β-adrenergic receptor antibodies from isolated blood, (i) wherein in a first step the presence or absence of an β-adrenergic receptor antibodies is determined in a sample, preferably a blood sample as defined herein, from a subject to be diagnosed for a chronic fatigue disease, like CFS or CRF, preferably CFS; and (ii) wherein, upon determining the presence of β-adrenergic receptor antibodies the antibody is removed from isolated blood of the subject. The blood may optionally been re-injected into the subject once the antibody are removed. Embodiments outlined herein above for the method of diagnosis, e.g. preferred β-adrenergic receptor antibodies, likewise apply to the method for removal of β-adrenergic receptor antibodies from isolated blood. For example preferred β-adrenergic receptor antibodies of the method are selected from the group consisting of β1-adrenergic receptor antibodies, β2-adrenergic receptor antibodies and β3-adrenergic receptor antibodies, preferably from the group consisting of β1-adrenergic receptor antibodies, and β2-adrenergic receptor antibodies.

The blood may be pretreated before the removal of said β-adrenergic receptor antibodies. Hence, in a preferred embodiment of the invention the plasma or serum is isolated from the isolated blood prior to removal of the β-adrenergic receptor antibodies, and β-adrenergic receptor antibodies are removed from said isolated plasma or serum.

Removal of β-adrenergic receptor antibodies may be performed selectively, i.e. only antibodies directed against β-adrenergic receptor are removed. However, it may be more feasible to remove total antibodies or subtypes of type of β-adrenergic receptor shall be applied to every method, kit or the like disclosed herein. The invention is further illustrated by the following non-limiting Examples and Figures.

| SEQUENCES |
|---|
| SEQ ID NO: 1:<br>Amino acid sequence of β1-adrenergic receptor [SEQ ID NO: 1]:<br>　　1　　　MGAGVLVLGA SEPGNLSSAA PLPDGAATAA RLLVPASPPA SLLPPASESP<br><br>　　51　　　EPLSQQWTAG MGLLMALIVL LIVAGNVLVI VAIAKTPRLQ TLTNLFIMSL<br><br>　101　　　ASADLVMGLL VVPFGATIVV WGRWEYGSFF CELWTSVDVL CVTASIETLC<br><br>　151　　　VIALDRYLAI TSPFRYQSLL TRARARGLVC TVWAISALVS FLPILMHWWR<br><br>　201　　　AESDEARRCY NDPKCCDFVT NRAYAIASSV VSFYVPLCIM AFVYLRVFRE<br><br>　251　　　AQKQVKKIDS CERRFLGGPA RPPSPSPSPV PAPAPPPGPP RPAAAAATAP<br><br>　301　　　LANGRAGKRR PSRLVALREQ KALKTLGIIM GVFTLCWLPF FLANVVKAFH<br><br>　351　　　RELVPDRLFV FFNWLGYANS AFNPIIYCRS PDFRKAFQGL LCCARRAARR<br><br>　401　　　RHATHGDRPR ASGCLARPGP PPSPGAASDD DDDDVVGATP PARLLEPWAG<br><br>　451　　　CNGGAAADSD SSLDEPCRPG FASESKV<br><br>SEQ ID NO: 2:<br>Amino acid sequence of β2-adrenergic receptor [SEQ ID NO: 2]:<br>　　1　　　MGQPGNGSAF LLAPNRSHAP DHDVTQQRDE VWVVGMGIVM SLIVLAIVFG<br><br>　　51　　　NVLVITAIAK FERLQTVTNY FITSLACADL VMGLAVVPFG AAHILMKMWT<br><br>　101　　　FGNFWCEFWT SIDVLCVTAS IETLCVIAVD RYFAITSPFK YQSLLTKNKA<br><br>　151　　　RVIILMVWIV SGLTSFLPIQ MHWYRATHQE AINCYANETC CDFFTNQAYA<br><br>　201　　　IASSIVSFYV PLVIMVFVYS RVFQEAKRQL QKIDKSEGRF HVQNLSQVEQ<br><br>　251　　　DGRTGHGLRR SSKFCLKEHK ALKTLGIIMG TFTLCWLPFF IVNIVHVIQD<br><br>　301　　　NLIRKEVYIL LNWIGYVNSG FNPLIYCRSP DFRIAFQELL CLRRSSLKAY<br><br>　351　　　GNGYSSNGNT GEQSGYHVEQ EKENKLLCED LPGTEDFVGH QGTVPSDNID<br><br>　401　　　SQGRNCSTND SLL | antibodies from the isolated blood. Hence, in a preferred embodiment of the method for the removal of β-adrenergic receptor antibodies from isolated blood, the removal step (ii) includes the removal of total antibodies from said isolated blood, serum or plasma. It may be preferred that the removal includes at least a type of antibodies. Hence, in one embodiment the removal step (ii) includes the removal of total IgG, IgM, IgA or IgE antibodies. As outlined herein, the identified β-adrenergic receptor antibodies in samples of CFS patients are of IgG types. Hence, in a particular preferred embodiment step (ii) at least includes the removal of total IgG antibodies from said isolated blood, serum or plasma. Means and methods for removing antibodies from isolated blood are commonly known by the skilled person and are commercially available and also referred to as immunapharesis (see e.g. Globaffin®, Fresenius Medical Care, Germany).

The invention also relates to a method for treating a chronic fatigue disease, preferably CRF or CFS, comprising the removal of antibodies directed against β-adrenergic receptor with a method according to the present invention.

It will be readily understood that the embodiments outlined above shall apply to the invention as a whole and not be limited to a specific method, unless stated otherwise. It will for example be understood the embodiments for the

EXAMPLES

Example 1

We measured the anti-β1-adrenergic receptor antibodies autoantibodies in serum samples using a sandwich ELISA kit. To this end, microtiter 96-well polystyrene plates were coated with a membrane extract of CHO cell cultures expressing human full length β1-adrenergic receptor antibodies of the sequence of SEQ ID NO: 1 using common techniques (e.g. see for AT1-Receptor ELISA Giral M, Foucher Y, Dufay A, Van Huyen J P, Renaudin K, Moreau A, Philippe A, Hegner B, Dechend R, Heidecke H, Brouard S, Cesbron A, Castagnet S, Devys A, Soulillou J P, Dragun D. Pretransplant sensitization against angiotensin II type 1 receptor is a risk factor for acute rejection and graft loss. Am J Transplant. 2013 October; 13(10):2567-76). Conformational epitopes of the receptor were maintained by addition of 1 mM calcium chloride to every buffer.

In order to obtain a standard curve, plates were incubated with test sera from an anti-β1-adrenergic receptor antibodies positive index patient suffering from systemic sclerosis. The ELISA was validated according to the FDA's "Guidance for industry: Bioanalytical method validation". anti-β1-adrenergic receptor-antibodies are not commercially available; a serum sample from a patient with a systemic sclerosis was used for the standard curve. A 1:800 dilution of the serum sample is defined as 40 units/ml anti-β1-adrenergic receptor antibodies. A 1:100 dilution of a healthy donor (not having an autoimmune disease) served as a negative control (range 2-6 units/ml). To set a standard for the concentrations of the autoimmune antibodies, a standard curve was generated. In detail, a serum sample of systemic sclerosis serum sample was diluted (a) 1:800 for standard point 40 units/ml, (b) 1:3200 for standard point 20 units/ml, (c) 1:12800 for standard point 10 units/ml, (d) 1:25600 for standard point 5 units/ml, and (e) 1:102400 for standard point 2.5 units/ml. Then the ratio of optical density at 450 nm and 620 nm was determined using the kit and method of above. Each standard point was performed in duplicates. Results are shown in FIG. 1.

To maintain the conformational epitopes of the protein/fragment, 1 mM calcium chloride was added to every buffer. Duplicates of a 1:100 dilution of all serum samples were incubated at 4° C. for 2 hours. After washing steps using, plates were incubated for 60 minutes with a 1:20.000 dilution of horseradish-peroxidase-labeled goat anti-human-IgG (Cat-No.: 109035008, Jackson, USA) used for detection.

Example 2

We measured the anti-β2-adrenergic receptor antibodies autoantibodies in serum samples using a sandwich ELISA kit. To this end, microtiter 96-well polystyrene plates were coated with a membrane extract of CHO cell cultures expressing human full length β2-adrenergic receptor antibodies of the sequence of SEQ ID NO: 2 using common techniques (e.g. see for AT1-Receptor ELISA Giral M, Foucher Y, Dufay A, Van Huyen J P, Renaudin K, Moreau A, Philippe A, Hegner B, Dechend R, Heidecke H, Brouard S, Cesbron A, Castagnet S, Devys A, Soulillou J P, Dragun D. Pretransplant sensitization against angiotensin II type 1 receptor is a risk factor for acute rejection and graft loss. Am J Transplant. 2013 October; 13(10):2567-76). Conformational epitopes of the receptor were maintained by addition of 1 mM calcium chloride to every buffer.

In order to obtain a standard curve, plates were incubated with test sera from an anti-β2-adrenergic receptor antibodies positive index patient suffering from systemic sclerosis. The ELISA was validated according to the FDA's "Guidance for industry: Bioanalytical method validation". anti-β2-adrenergic receptor-antibodies are not commercially available; a serum sample from a patient with a systemic sclerosis was used for the standard curve. A 1:4000 dilution of the serum sample is defined as 40 units/ml anti-β2-adrenergic receptor antibodies. A 1:100 dilution of a healthy donor (not having an autoimmune disease) served as a negative control (range 2-6 Units/ml). To set a standard for the concentrations of the autoimmune antibodies, a standard curve was generated. In detail, a serum sample of systemic sclerosis serum sample was diluted (a) 1:4000 for standard point 40 units/ml, (b) 1:8000 for standard point 20 units/ml, (c) 1:16000 for standard point 10 units/ml, (d) 1:24000 for standard point 5 units/ml, and (e) 1:84000 for standard point 2.5 units/ml. Then the ratio of optical density at 450 nm and 620 nm was determined using the kit and method of above. Each standard point was performed in duplicates. Results are shown in FIG. 1.

Example 3

Figure 3:
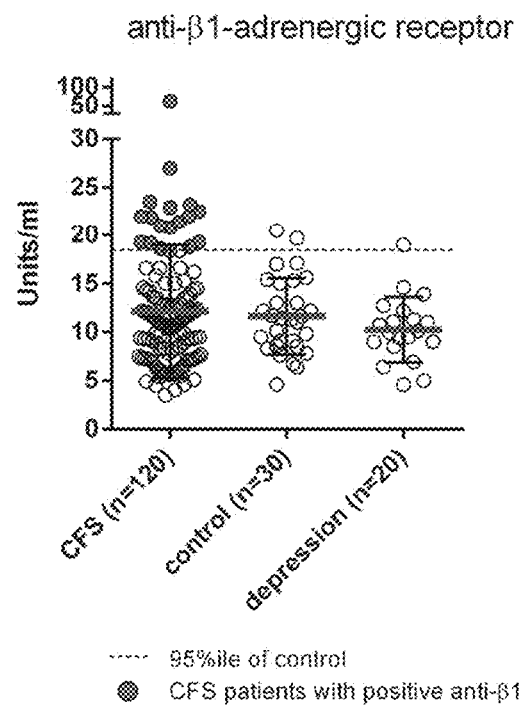
FIG. 3: (A) Levels of antibodies directed against β1-adrenergic receptor (β1-R) in patients suffering from chronic fatigue syndrome (n=120), healthy controls (control, n=30)), and patients suffering from a depression (n=20). (B) Levels of antibodies directed against β2-adrenergic receptor (β2-R) in patients suffering from chronic fatigue syndrome, healthy controls (control), and patients suffering from a depression. Dotted line indicates 95$^{th}$ percentile of healthy controls.
Figure 3:
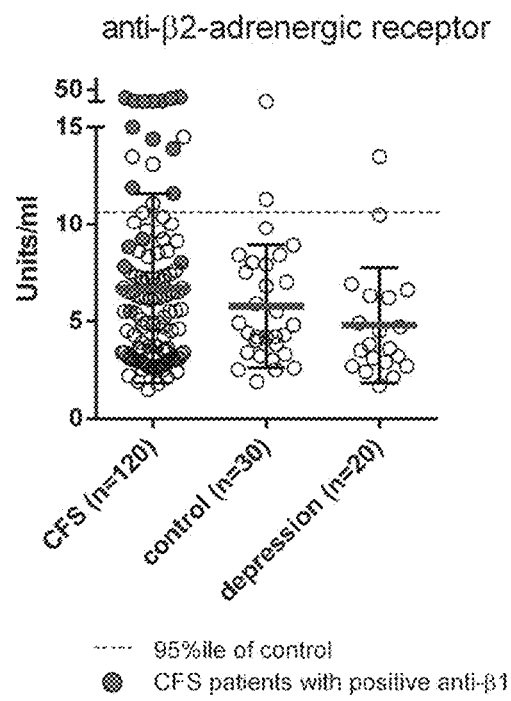
Figure 4:
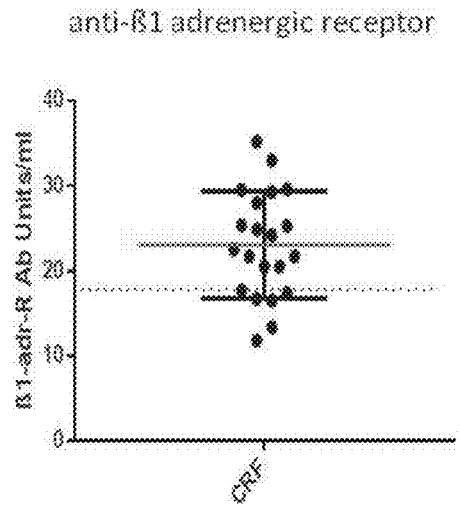
FIG. 4: (A) Levels of antibodies directed against β1-adrenergic receptor (β1-adr-R Ab) in patients suffering from chronic cancer-related fatigue (n=21). (B) Levels of antibodies directed against β2-adrenergic receptor (β2-adr-R Ab) in patients suffering from chronic fatigue syndrome, healthy controls (control), and patients suffering from a depression. Dotted line indicates 95$^{th}$ percentile of healthy controls.
Figure 4:
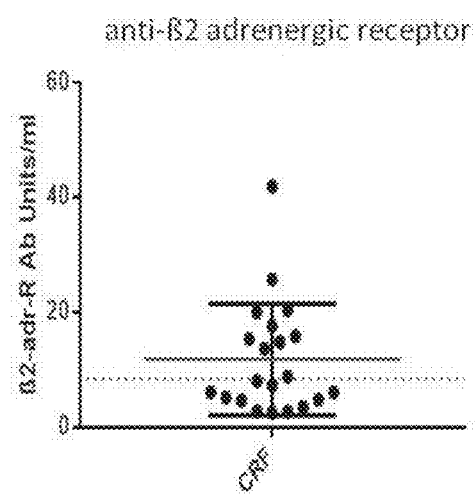

Anti-β1-adrenergic receptor antibodies and anti-β2-adrenergic receptor antibodies levels were measured using the assays of Examples 1 and 2, respectively. Measurement was performed in serum samples from 30 healthy donors ("control"), 20 patients having depression, 120 patients suffering from CFS, and 2 patients suffering from chronic cancer related fatigue. Results for healthy donors and CFS are given in FIG. 3, results for CRF in FIG. 4.

The analysis revealed that when setting a cut-off of >95$^{th}$ percentile of healthy controls, 17 and 16 of the 120 CFS patients showed the presence of anti-β1-adrenergic receptor antibodies and anti-β2-adrenergic receptor antibodies, respectively; and 15 and 9 of the 21 CRF patients showed the presence of anti-β1-adrenergic receptor antibodies and anti-β2-adrenergic receptor antibodies, respectively. 11 CFS patients showed the presence of both antibodies, 6 CFS patients had ß1 and 5 CFS patients ß2 antibodies only. This means that 17.5% of CFS patients showed increased anti-β adrenergic receptor antibodies. 9 CRF patients showed the presence of both, anti-β1 and anti-β2 antibodies, 6 CRF patients had ß1 antibody only. This means that 71% of CRF patients showed increased anti-β adrenergic receptor antibodies.

The results of the present Examples show that levels of anti-β1-adrenergic receptor antibodies and anti-β2-adrenergic receptor antibodies are significant higher in patients with CFS compared to healthy controls or patients suffering from a depression. This data fits with the current concept that CFS is a heterogenous disease and suggests that autoantibodies to other targets are found in other CFS patients. So far another subgroup of approx. 20% of CFS patients was already shown to have autoantibodies to muscarinic anticholinergic receptors.

The presence of ß-adrenergic receptor autoantibodies is a biomarker indicating the requirement of a therapy. Furthermore, immunoadsorption is effective to treat patients with autoantibody-mediated autoimmune diseases. The data clearly shows the chronic fatigue diseases being autoimmune driven in at least a subgroup of patients. Hence, the patients showing the autoantibodies would profit from a removal of the autoantibodies from their blood.

In context with CFS the invention in particular relates to the following items:
1. A method for diagnosis chronic fatigue syndrome (CFS) in a subject, comprising the step of
   determining the presence or absence of antibodies directed against one or more β-adrenergic receptor in a sample of the subject to be diagnosed,
   wherein the presence of antibodies directed against β-adrenergic receptor is indicative of CFS in said subject.
2. The method for diagnosis of CFS according to item 1, wherein the step of determining the presence or absence of antibodies directed against one or more β-adrenergic receptor comprises the steps of:
   (i) determining the level of antibodies directed against one or more β-adrenergic receptor in a sample from a subject to be diagnosed,
   (ii) comparing the determined level in the sample to a control level of β-adrenergic receptor antibodies derived from one or more subjects without CFS;
   wherein an increased level in the sample from the subject to be diagnosed as compared to the control level is attributed to the presence of antibodies directed against one or more β-adrenergic receptor and is indicative of CFS in the subject to be diagnosed.
3. The method for diagnosing of CFS according to item 1 or 2, wherein said one or more β-adrenergic receptor is selected from the group consisting of β1-adrenergic receptor and β2-adrenergic receptor.
4. The method of any one of items 1 to 3, wherein the β-adrenergic receptor antibodies are IgG antibodies.
5. The method for diagnosis of CFS according to any one of items 2 to 4, wherein a level of β-adrenergic receptor antibodies in the sample of the patient to be diagnosed of more than 1.5 fold as compared to the control level is indicative of the presence of a β-adrenergic receptor in the sample and for the presence of CFS in the subject to be diagnosed.
6. The method for diagnosis of CFS according to any one of items 1 to 5, wherein a level of antibodies directed against β1-adrenergic receptor above 10 units/ml is indicative of CFS in said subject, and/or wherein a level of antibodies directed against β2-adrenergic receptor above 5 units/ml is indicative of CFS in said subject to be diagnosed.
7. The method according to any one of items 1 to 6, wherein said β-adrenergic receptor antibodies are detected in an immunoassay.
8. The method according to item 7, wherein the immunoassay is selected from the group of immunoprecipitation, enzyme immunoassay (EIA), radioimmunoassay (RIA), enzyme-linked immunosorbent assay (ELISA), fluorescent immunoassay, a chemiluminescent assay, an agglutination assay, nephelometric assay, turbidimetric assay, a Western Blot, a competitive immunoassay, a noncompetitive immunoassay, a homogeneous immunoassay a heterogeneous immunoassay, a bioassay and a reporter assay such as a luciferase assay or luminex.
9. The method according to any one of the preceding items, wherein the sample is plasma or serum.
10. The method according to any one of the preceding items, comprising the steps of
    (a) contacting the sample with a β-adrenergic receptor or an antigenic peptide fragment thereof under conditions allowing for the formation of a complex between anti-β-adrenergic receptor antibodies with the β-adrenergic receptor or said antigenic peptide fragment thereof; and
    (b) detecting the complex.
11. The method of item 10, wherein the β-adrenergic receptor or the antigenic peptide fragment thereof is immobilized on a surface.
12. The method according to any one of items 10 or 11, wherein the complex is detected using a secondary antibody against the Fc portion of the β-adrenergic receptor.
13. The method according to any one of items 10 to 12, wherein the β-adrenergic receptor antibody is an IgG antibody and the secondary antibody is an anti-IgG-antibody.
14. The method according to item 12 or 13, wherein the secondary antibody is labeled with a detectable marker.
15. A kit for diagnosing CFS, said kit comprising a β-adrenergic receptor or an antigenic peptide thereof.
16. The kit according to item 15, wherein the kit comprises β1-adrenergic receptor or an antigenic peptide thereof and β2-adrenergic receptor or an antigenic peptide thereof.
17. The kit according to item 15 or 16, where the kit additionally comprises means to detect antibodies binding to said β-adrenergic receptor or said antigenic peptide thereof.
18. The kit according to item 17, wherein said means to detect said antibodies are means to detect IgG-antibodies, preferably said means are antibodies or fragments thereof binding to the Fc portion of an IgG-antibody.
19. Use of β-adrenergic receptor or an antigenic peptide thereof, or of a kit according to any one of items 15 to 18 for the diagnosis of CFS.
20. The use according to item 19, wherein said β-adrenergic receptor or an antigenic peptide thereof is used for detection of β-adrenergic receptor antibodies in a sample of the subject to be diagnosed.
21. A method for the removal of β-adrenergic receptor antibodies from isolated blood, comprising the steps of:
    (i) determining in a sample of a subject the presence or absence of an β-adrenergic receptor antibodies is determined in a sample
    (ii) removing β-adrenergic receptor antibodies from isolated blood of the subject.
22. The method according to item 21, wherein the subject is a subject to be diagnosed for the presence of CFS.
23. The method according to item 21 or 22, wherein the plasma or serum is isolated from the isolated blood prior to removal of the β-adrenergic receptor antibodies, and wherein β-adrenergic receptor antibodies are removed from said isolated plasma or serum.
24. The method according to any one of items 21 to 23, wherein step (ii) includes the removal of total antibodies from said isolated blood, serum or plasma, preferably the removal of total IgG, IgM, IgA or IgE antibodies, preferably step (ii) includes the removal of total IgG antibodies from said isolated blood, serum or plasma.

The invention claimed is:

1. A method for detecting an autoantibody that binds to one or more β-adrenergic receptors, the method comprising:
providing a sample from a mammal selected from the group consisting of blood, serum, plasma, cerebrospinal fluid, saliva, urine, sputum, and pleural effusion;
detecting in said sample an autoantibody that binds to one or more β-adrenergic receptors selected from the group consisting of β1-adrenergic receptor, β2-adrenergic receptor, and β3-adrenergic receptor;
determining the level of the autoantibody in said sample;
detecting, in control samples obtained from mammals without a chronic fatigue disease or with depression, an autoantibody that binds to one or more β-adrenergic receptors selected from the group consisting of β1-adrenergic receptor, β2-adrenergic receptor, and β3-adrenergic receptor;
determining the 90th percentile of the control autoantibody level in said control samples; and
determining whether the determined autoantibody level is greater than the 90th percentile of the control autoantibody level.

2. The method according to claim 1, wherein said one or more β-adrenergic receptor is selected from the group consisting of β1-adrenergic receptor and β2-adrenergic receptor.

3. The method of claim 1, wherein the β-adrenergic receptor autoantibodies are IgG antibodies.

4. The method according to claim 1, wherein the chronic fatigue disease is selected from the group consisting of chronic fatigue syndrome (CFS) and chronic cancer-related fatigue (CRF).

5. The method according to claim 1, wherein said autoantibodies are detected in an immunoassay.

6. The method according to claim 5, wherein the immunoassay is selected from the group of immunoprecipitation, enzyme immunoassay (EIA), radioimmunoassay (RIA), enzyme-linked immunosorbent assay (ELISA), fluorescent immunoassay, a chemiluminescent assay, an agglutination assay, nephelometric assay, turbidimetric assay, a Western Blot, a competitive immunoassay, a noncompetitive immunoassay, a homogeneous immunoassay a heterogeneous immunoassay, a bioassay and a reporter assay optionally a luciferase assay or luminex.

7. The method according to claim 1, wherein the sample from the mammal is plasma or serum.

8. The method according to claim 1, the step of detecting comprising:
(a) contacting the sample from the mammal with a β-adrenergic receptor or an antigenic peptide fragment thereof under conditions allowing for the formation of a complex between anti-β-adrenergic receptor antibodies with the β-adrenergic receptor or said antigenic peptide fragment thereof; and
(b) detecting the complex.

9. The method of claim 8, wherein the β-adrenergic receptor or the antigenic peptide fragment thereof is immobilized on a surface.

10. The method according to claim 8, wherein the β-adrenergic receptor antibody is an IgG antibody and the secondary antibody is an anti-IgG-antibody.

11. The method according to claim 10, wherein the secondary antibody is labeled with a detectable marker.

* * * * *

SEQUENCE LISTING

```
<160> NUMBER OF SEQ ID NOS: 2

<210> SEQ ID NO 1
<211> LENGTH: 477
<212> TYPE: PRT
<213> ORGANISM: Homo sapiens
<220> FEATURE:
<221> NAME/KEY: MISC_FEATURE
<222> LOCATION: (1)..(477)
<223> OTHER INFORMATION: Amino acid sequence of 1-adrenergic receptor

<400> SEQUENCE: 1

Met Gly Ala Gly Val Leu Val Leu Gly Ala Ser Glu Pro Gly Asn Leu
1               5                   10                  15
```

-continued

Ser Ser Ala Ala Pro Leu Pro Asp Gly Ala Ala Thr Ala Ala Arg Leu
        20                  25                  30

Leu Val Pro Ala Ser Pro Ala Ser Leu Leu Pro Pro Ala Ser Glu
    35                  40                  45

Ser Pro Glu Pro Leu Ser Gln Gln Trp Thr Ala Gly Met Gly Leu Leu
50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
            85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
    115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
            165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
    195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
            245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
    275                 280                 285

Pro Pro Arg Pro Ala Ala Ala Ala Thr Ala Pro Leu Ala Asn Gly
    290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
            325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
    355                 360                 365

Asn Ser Ala Phe Asn Pro Ile Ile Tyr Cys Arg Ser Pro Asp Phe Arg
370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
            405                 410                 415

Arg Pro Gly Pro Pro Pro Ser Pro Gly Ala Ala Ser Asp Asp Asp Asp
    420                 425                 430

Asp Asp Val Val Gly Ala Thr Pro Pro Ala Arg Leu Leu Glu Pro Trp

```
              435                 440                 445
Ala Gly Cys Asn Gly Gly Ala Ala Ala Asp Ser Asp Ser Ser Leu Asp
            450                 455                 460

Glu Pro Cys Arg Pro Gly Phe Ala Ser Glu Ser Lys Val
465                 470                 475

<210> SEQ ID NO 2
<211> LENGTH: 413
<212> TYPE: PRT
<213> ORGANISM: Homo sapiens
<220> FEATURE:
<221> NAME/KEY: MISC_FEATURE
<222> LOCATION: (1)..(413)
<223> OTHER INFORMATION: Amino acid sequence of 2-adrenergic receptor

<400> SEQUENCE: 2

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320
```

```
Phe Asn Pro Leu Ile Tyr Cys Arg Ser Pro Asp Phe Arg Ile Ala Phe
            325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
            355                 360                 365

Glu Gln Glu Lys Glu Asn Lys Leu Leu Cys Glu Asp Leu Pro Gly Thr
        370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
            405                 410
```